(12) United States Patent
Mizoguchi et al.

(10) Patent No.: US 9,756,315 B2
(45) Date of Patent: Sep. 5, 2017

(54) ENDOSCOPIC SYSTEM TO DISPLAY THREE-DIMENSIONAL PICTURE

(71) Applicant: OLYMPUS CORPORATION, Tokyo (JP)

(72) Inventors: Masakazu Mizoguchi, Hachioji (JP); Hiroshi Ushiroda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/873,488

(22) Filed: Oct. 2, 2015

(65) Prior Publication Data

US 2016/0029011 A1 Jan. 28, 2016

Related U.S. Application Data

(63) Continuation of application No. PCT/JP2014/059736, filed on Apr. 2, 2014.

(30) Foreign Application Priority Data

Apr. 3, 2013 (JP) .................................. 2013-078071

(51) Int. Cl.
*H04N 13/02* (2006.01)
*A61B 1/00* (2006.01)
(Continued)

(52) U.S. Cl.
CPC ....... *H04N 13/0296* (2013.01); *A61B 1/0002* (2013.01); *A61B 1/00006* (2013.01);
(Continued)

(58) Field of Classification Search
CPC ........... H04N 13/0296; H04N 13/0022; H04N 13/0044; H04N 13/0055; H04N 13/0203;
(Continued)

(56) References Cited

U.S. PATENT DOCUMENTS

2012/0281064 A1* 11/2012 Holloway .......... H04N 13/0022
348/43

FOREIGN PATENT DOCUMENTS

JP          06254046 A  *  9/1994
JP       H06-245233 A      9/1994
(Continued)

OTHER PUBLICATIONS

English translation of International Preliminary Report on Patentability dated Oct. 15, 2015 together with the Written Opinion, received in related International Application No. PCT/JP2014/059736.
International Search Report dated Jul. 8, 2014 issued in PCT/JP2014/059736.
Japanese Office Action dated Mar. 3, 2015 issued in JP 2014-559973.
Extended Supplementary European Search Report dated Dec. 8, 2016 in related European Patent Application No. 14 78 0347.2.

*Primary Examiner* — Gims Philippe
*Assistant Examiner* — On S Mung
(74) *Attorney, Agent, or Firm* — Scully, Scott, Murphy & Presser, P.C.

(57) ABSTRACT

A picture switch is performed to select a right picture and a left picture, a right picture and a right picture, or a left picture and a left picture without changing the kind and format of a video signal before and after a switch of a 2D picture and a 3D picture of an endoscopic system, and a picture shift is performed to horizontally shift the right picture and the left picture, and the pictures are then output to a monitor.

8 Claims, 9 Drawing Sheets

(51) Int. Cl.
*A61B 1/045* (2006.01)
*H04N 13/00* (2006.01)
*H04N 5/225* (2006.01)

(52) U.S. Cl.
CPC ...... *A61B 1/00009* (2013.01); *A61B 1/00045* (2013.01); *A61B 1/00193* (2013.01); *A61B 1/045* (2013.01); *H04N 13/0022* (2013.01); *H04N 13/0044* (2013.01); *H04N 13/0055* (2013.01); *H04N 13/0203* (2013.01); *H04N 13/026* (2013.01); *H04N 2005/2255* (2013.01)

(58) Field of Classification Search
CPC . A61B 1/0002; A61B 1/0052; A61B 1/00064; A61B 1/042; A61B 1/00193; A61B 1/00131; A61B 1/00071; A61B 1/045
USPC .......................................................... 348/45
See application file for complete search history.

(56) References Cited

FOREIGN PATENT DOCUMENTS

| | | |
|---|---|---|
| JP | H06-254046 A | 9/1994 |
| JP | H09-5643 A | 1/1997 |
| JP | H09-9300 A | 1/1997 |
| JP | H10-248807 A | 9/1998 |
| JP | H10-285613 A | 10/1998 |
| JP | 2003-260028 A | 9/2003 |
| JP | 2012-249168 A | 12/2012 |

\* cited by examiner

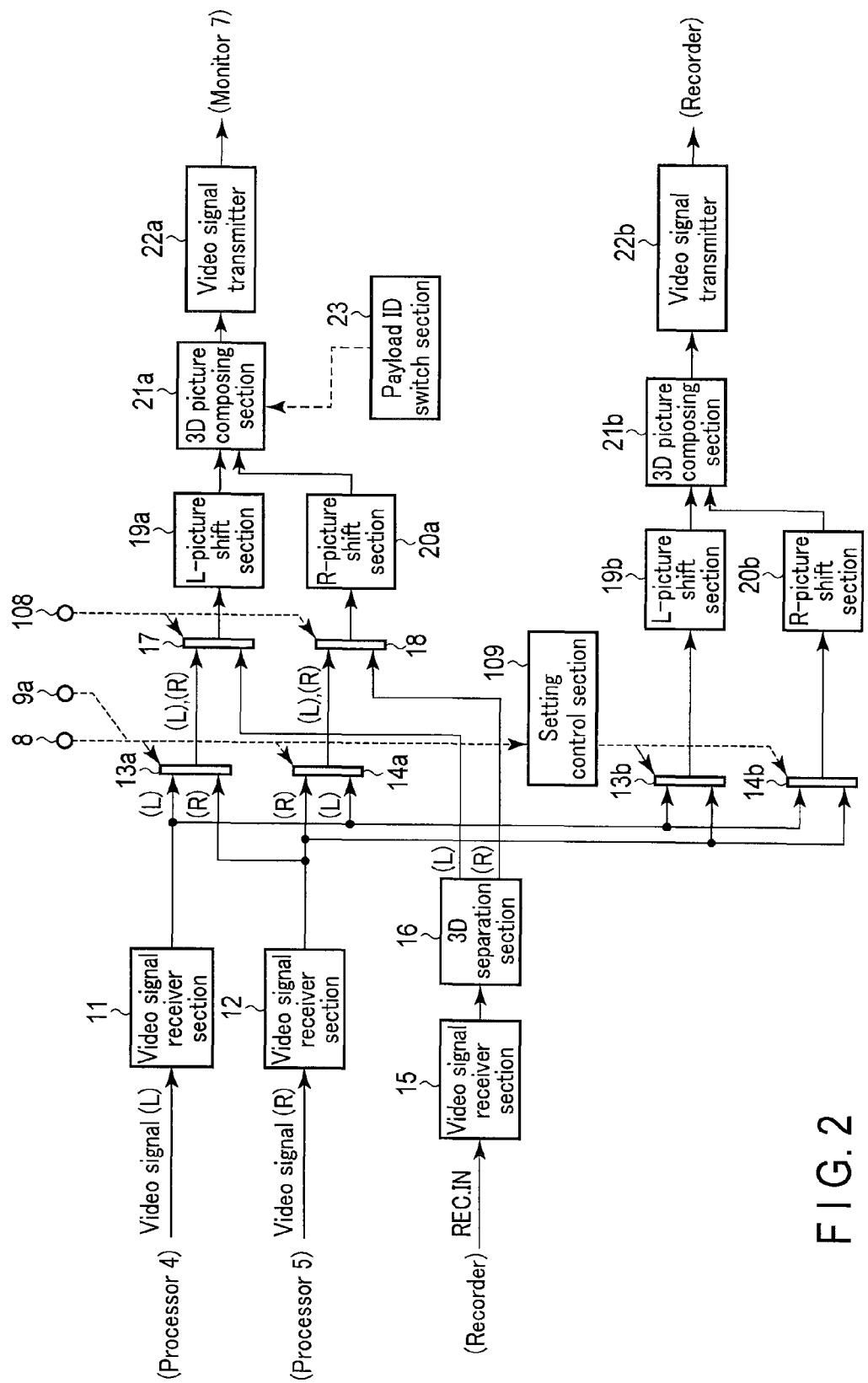
F I G. 2

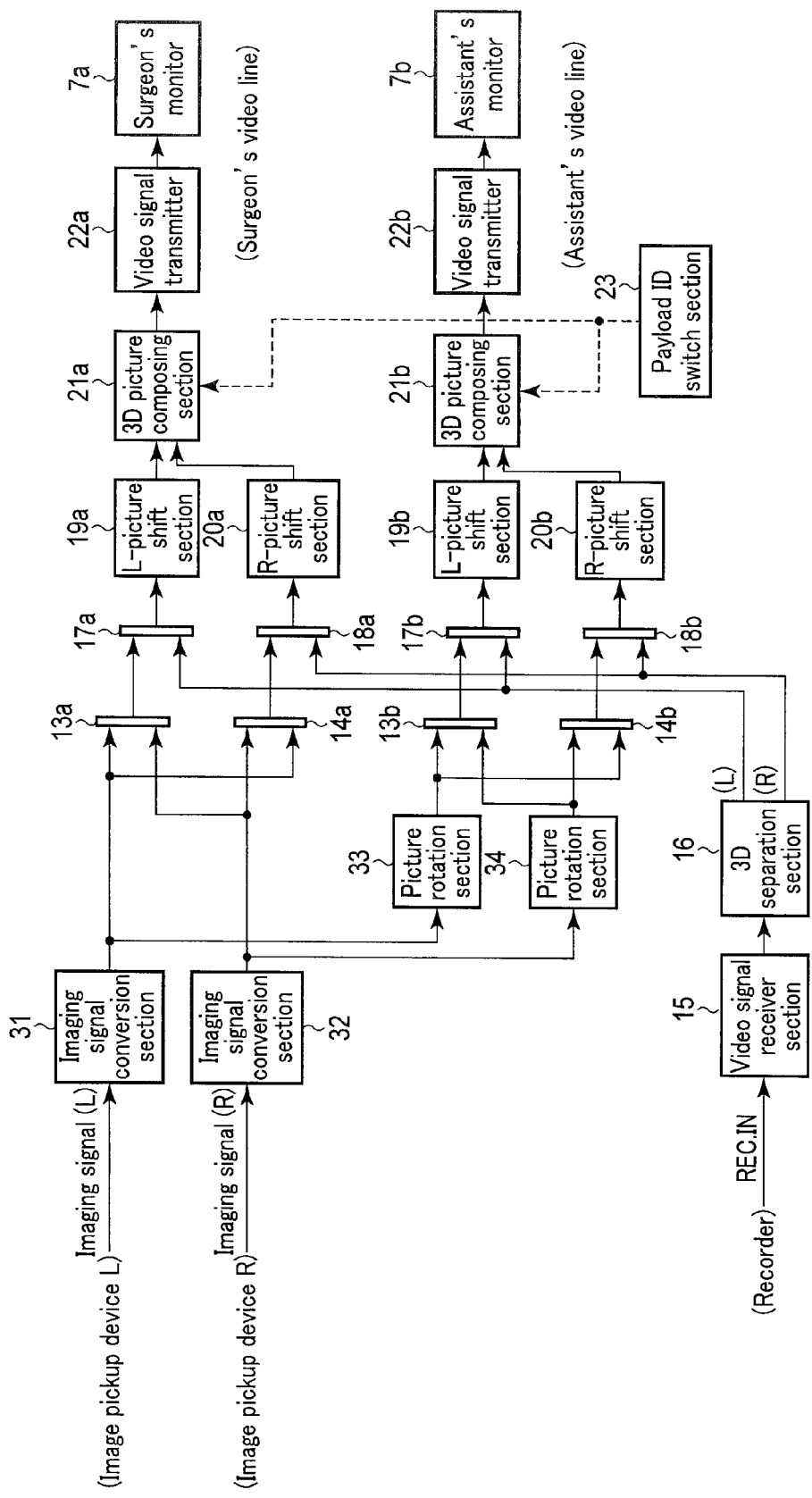
F I G. 8

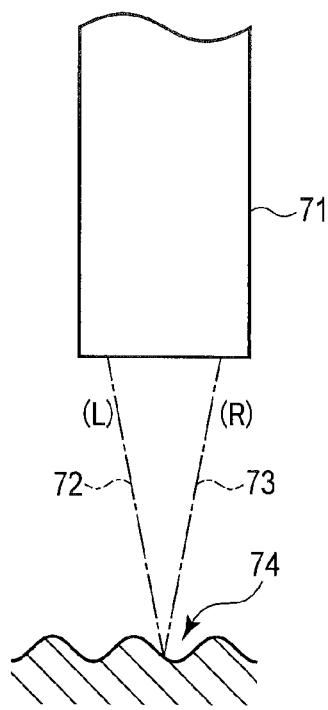
F I G. 9A
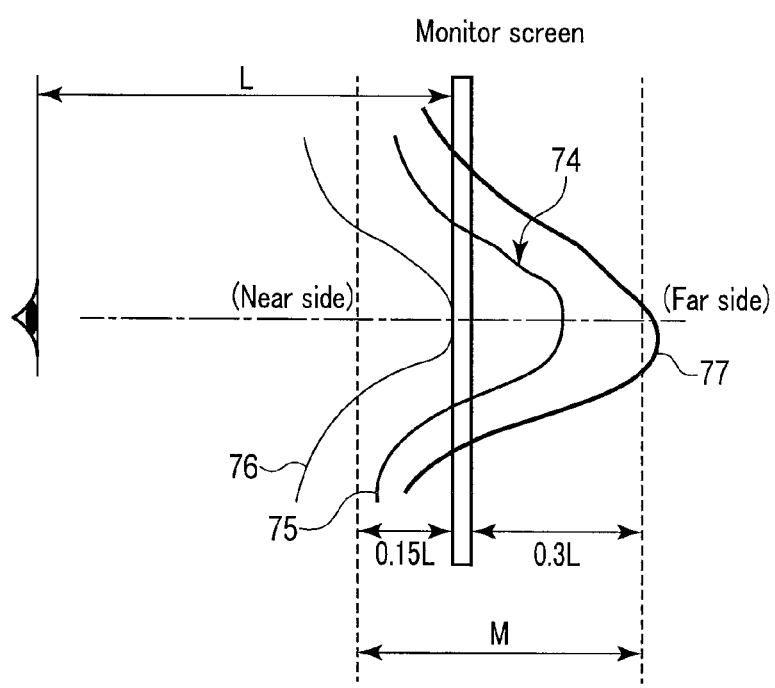
F I G. 9B

ENDOSCOPIC SYSTEM TO DISPLAY THREE-DIMENSIONAL PICTURE

CROSS-REFERENCE TO RELATED APPLICATIONS

This is a Continuation Application of PCT Application No. PCT/JP2014/059736, filed Apr. 2, 2014, which was published under PCT Article 21(2) in Japanese.

This application is based upon and claims the benefit of priority from prior the Japanese Patent Application No. 2013-078071, filed Apr. 3, 2013 the entire contents of which are incorporated herein by references.

BACKGROUND OF THE INVENTION

1. Field of the Invention

The present invention relates to an endoscopic system for the display of a three-dimensional picture which displays a picture taken as a stereoscopic picture in a body cavity so that the picture can be switched to a planar picture (two-dimensional picture: 2D) or a stereoscopic picture (three-dimensional picture: 3D).

2. Description of the Related Art

Recently, in display devices such as televisions, devices which can display stereoscopic pictures (3D pictures) showing a feeling of depth therein have been coming into wide use. Current endoscopic devices generally display planar pictures (2D pictures). An observational diagnosis or treatment operation is performed with an estimated or experiential sense of distance for an observation spot and the operation of a treatment instrument such as a forceps that are shown on a screen simultaneously with the observation of displayed images taken by a photography section at the distal end of an endoscope. Thus, there have been demands from users including surgeons for the reduction of the burden of the operation associated with the stereoscopic pictures to supplement the sense of distance.

A naked-eye-type method for observing 3D pictures with the naked eye has been suggested as one known video method for 3D pictures. According to this method, the positions to stand before a display screen are extremely limited. Thus, video methods for 3D pictures by monitor observation that are mostly used are naked-eye-type methods using polarized glasses or liquid-crystal shutter glasses. Among these methods, the method that uses the polarized glasses is the mainstream method in medical fields where more than one monitor are disposed in many cases.

The above-mentioned 3D pictures allow a feeling of depth of an observation spot to be obtained and are therefore suitable to the observation of the inside of a body cavity. However, 2D planar pictures may be easier to view depending on display contents, for example, when an observation object is located extremely close or when a treatment instrument or an organ which is not an observation object is located extremely close. Jpn. Pat. Appln. KOKAI Publication No. 2012-249168 suggests a technique for switching between a 3D picture and a 2D picture.

The presence of a switching time is a challenge in the switch between a 3D picture and a 2D picture. That is, the original picture on a monitor screen disappears when a switching operation is performed with a switch, and a switched picture is displayed after a time. That is, in the case of a switch from a 3D picture to a 2D picture and vice versa, there may be a slight time in which the display is off. This is because when the format of a video signal to be input is switched, the monitor first detects a format, and then receives video data to be displayed on the basis of the detected format. However, if the screen turns off even for a slight period during the operation of the endoscopic device, the efficiency of treatment or diagnosis deteriorates, and the burden on a surgeon or a patient increases.

It is therefore an object of the present invention to provide an endoscopic system capable of switching between a 3D picture and a 2D picture in which a screen non-display time during the switch between a 3D picture and a 2D picture is reduced.

BRIEF SUMMARY OF THE INVENTION

According to an embodiment of the present invention, there is provided an endoscopic system comprising: an endoscope configured to acquire each of right-eye and left-eye optical images to generate right-eye and left-eye video signals which indicate the respective right-eye and left-eye optical images; a mixer section to which each of the video signals is input from the endoscope; and a switch section which selects whether to output both of the right-eye and left-eye video signals or one of the right-eye and left-eye video signals from the mixer section, wherein the mixer section comprises a first selector which outputs one of the right-eye video signal and the left-eye video signal in accordance with a selection operation by the switch section, a second selector which outputs one of a video signal different from the video signal selected by the first selector and the same video signal as the video signal selected by the first selector to the right-eye video signal video signal and the left-eye video signal in accordance with the selection operation in the switch section, a picture shift section which processes each of the video signals output from the first selector and the second selector so that a picture represented by each of the video signals is horizontally shifted on the basis of a given shift value, and a picture output section which converts a video signal output from the picture shift section into a predetermined stereoscopic video signal format regardless of the selection operation in the switch section, and then outputs the video signal to a stereoscopic picture display apparatus.

According to the present invention, it is possible to provide an endoscopic system for the display of a three-dimensional picture in which a screen non-display time during the switch between a 3D picture and a 2D picture is reduced.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a diagram showing a configuration example of a video mixer unit which performs video processing and display according to a first embodiment;

FIG. 8 is a diagram showing a configuration example of a video mixer unit which performs video processing and display according to a sixth embodiment;

FIG. 9A is a diagram illustrating an easily viewable observation image by a 3D picture according to an eighth embodiment;

FIG. 9B is a diagram illustrating the easily viewable observation image by a 3D picture according to the eighth embodiment;

DETAILED DESCRIPTION OF THE PREFERRED EMBODIMENT

Hereinafter, embodiments of the present invention will be described in detail with reference to the drawings.

First Embodiment

Figure 1A:
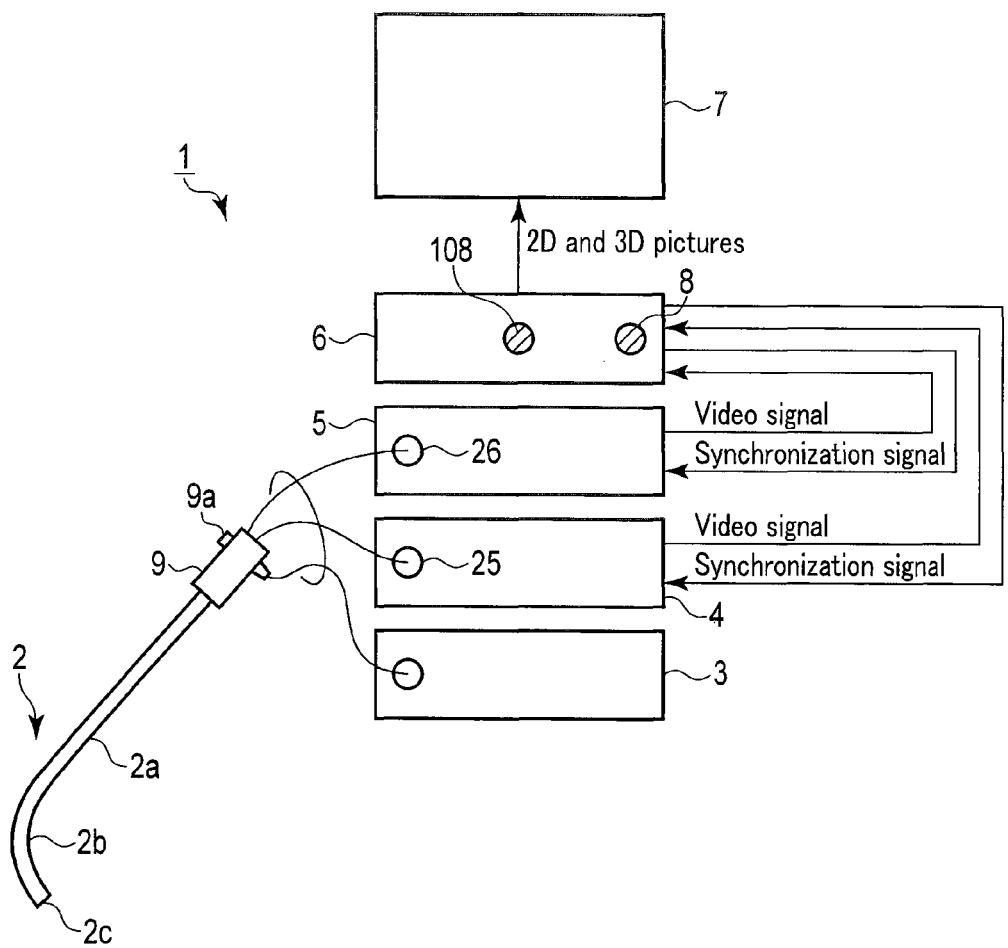
FIG. 1A is a block diagram showing the schematic configuration of the whole endoscopic system according to an embodiment of the present invention.
Figure 1B:
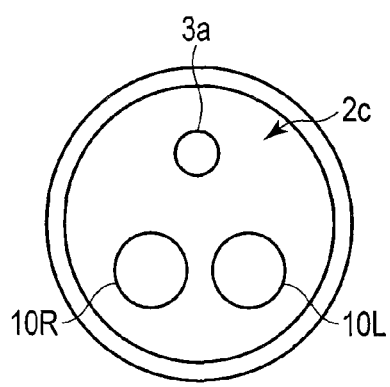
FIG. 1B is a diagram showing an arrangement example of a photography unit and an illumination window at the distal end of an insertion portion.

FIG. 1A is a block diagram showing the schematic configuration of the whole endoscopic system according to an embodiment of the present invention. FIG. 1B is a diagram showing an arrangement example of a photography unit and an illumination window at the distal end of an insertion portion. The endoscope body 2 is a flexible scope by way of example in the present embodiment, but may be a rigid scope.

An endoscopic system 1 according to the present embodiment comprises the endoscope body (known as a stereoscopic endoscope) 2 capable of taking 3D pictures (stereoscopic pictures or three-dimensional pictures), a light source unit 3 which generates illumination light for observation and photography, a first processor 4 which subjects a picture (L-picture) projected to the left eye to video processing, a second processor 5 which subjects a picture (R-picture) projected to the right eye to video processing, a video mixer unit (third processor) 6 which records, composes, and separates the L-picture and the R-picture and which switches between 2D and 3D, and a monitor (video display section) 7 which displays the 2D or 3D pictures.

The endoscope body 2 comprises an insertion portion 2a which is inserted into a body cavity to be an observation object, a curving portion 2b provided at the distal end of the insertion portion 2a, and an operation portion 9 which curves the curving portion 2b. Two photography units 10L and 10R which are photography sections and an illumination window 3a which emits illumination light are provided on a distal end face 2c of the insertion portion 2a. Although the configuration is not shown, each of the photography units 10L and 10R comprises an objective lens serving as an observation window exposed in the distal end face 2c, an imaging lens system disposed on an optical axis to follow the objective lens, and a photography element (e.g. a Charge Coupled Device) which generates a video signal by photoelectrically converting an observation image formed by the imaging lens system. A stereoscopic video photography unit is formed by the two photography units 10L and 10R.

In addition to operation buttons for various operations, a 3D/2D picture changeover switch (hereinafter, a changeover switch) 9a is provided in the operation portion 9. This changeover switch 9a is a manual switch for a surgeon to instruct to switch the display of a 3D picture and a 2D picture on the monitor 7 described later.

Furthermore, the light source unit 3 is coupled to the illumination window 3a by a light guide comprising optical fibers, and the illumination light is guided to the illumination window 3a. The endoscope body 2 is connected to each processor and each unit by a universal cable through a connector. The cable includes a light guide and signal lines to transmit video signals and others. A supply path (gas/liquid supply channel) and a discharge path comprising tubes for introducing a gas and a liquid for cleaning the observation window and the illumination window may be provided in the universal cable.

The signal lines for the L/R video signals output from the endoscope body 2 are connected to the two L/R scope connectors 25 and 26 through the universal cable. The L scope connector 25 is attached and electrically connected to the first processor 4, and the R scope connector 26 is attached and electrically connected to the second processor 5.

The first processor 4 and the second processor 5 have known configurations for video processing, and subject signals of the L and R photography units obtained by the photography units 10L and 10R to video processing, and convert the signals to video signals. The L and R video signals which have been subjected to the video processing are synchronized in accordance with a synchronization signal communicated between the video mixer unit 6 and the first processor 4 as well as the second processor 5, and output to the video mixer unit 6 from the first processor 4 and the second processor 5.

FIG. 2 is a diagram showing a configuration example of the video mixer unit 6 which performs video processing and display according to the first embodiment. In the following explanation, a and, b that are given to the reference signs of the respective components except for the reference sign 9a signify equivalent components.

The video mixer unit 6 is configured to receive video input signals from the processor 4, the processor 5, and an unshown recorder by three video signal receiver sections 11, 12, and 15, respectively. For the video input signal from the recorder, a 3D separation section 16 is configured to be able to separate a reproduction picture by the recorder into a right picture and a left picture.

Next, a configuration of video output for the monitor is described.

The video signal receiver sections 11 and 12 are connected to a pair of selectors 13a and 14a, and input the respective received pictures to the selectors 13*a* and 14*a*. The selectors 13*a* and 14*a* are respectively connected to selectors 17 and 18, and the pictures selected by the selectors 13*a* and 14*a* are input to the selectors 17 and 18. The later-described 3D separation section 16 are connected to the input sides of the selectors 17 and 18, and switched to the input of one of the side of the selectors 13*a* and 14*a* and the side of the 3D separation section 16 by an input switch 108.

As a result of this input switch, endoscope pictures from the first processor 4 and the second processor 5 are selected or a video input from the unshown recorder is selected, and output to the monitor 7. The input switch 108 is provided in an operation panel of the video mixer unit 6.

The selector 17*a* is connected to an L-picture shift section 19*a*, and the selector 18 is connected to an R-picture shift section 20*a*. The respective pictures selected by the selectors 17 and 18 are input to the L-picture shift section 19*a* and the R-picture shift section 20*a*.

The L-picture shift section 19*a* and the R-picture shift section 20*a* are further connected to a 3D picture composing section 21*a*. The 3D picture composing section 21*a* arranges data for the right picture and the left picture in accordance with a video signal to be output and a 3D format.

The video signal of the picture composed by the 3D picture composing section 21*a* is output to the connected monitor 7 via a video signal transmitter 22*a* connected to the 3D picture composing section 21*a*.

Next, a configuration of video output for the recorder is described.

The video signal receiver sections 11 and 12 are connected to a pair of selectors 13*b* and 14*b*, and the respective pictures received by the video signal receiver sections 11 and 12 are input to the pair of selectors 13*a* and 14*a*. The pictures selected by the selectors 13*b* and 14*b* are input to an L-picture shift section 19*b* and an R-picture shift section 20*b*, and are provided with video shifts corresponding to a recording output.

The L-picture shift section 19*b* and the R-picture shift section 20*b* are further connected to a 3D picture composing section 21*b*. The 3D picture composing section 21*b* arranges data for the right picture and the left picture in accordance with a video signal corresponding to the unshown recorder and a 3D format.

Here, the video mixer unit 6 is provided with the changeover switch 9*a* which is provided in the operation portion 9 of the endoscope body 2, and a similar manual 3D/2D picture changeover switch (hereinafter, a changeover switch) 8 for instructing to switch the display of a 3D picture and a 2D picture. The switch 9*a* and the changeover switch 8 are connected to the selectors 13*a* and 14*a* and a setting control section 109.

Figure 3:
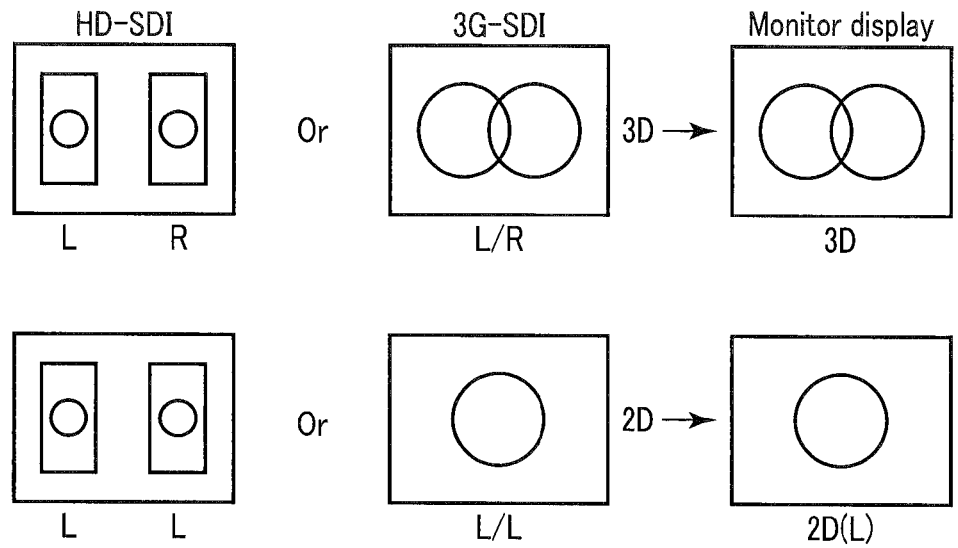
FIG. 3 is a diagram schematically showing a transmission method for a 3D picture and a 2D picture.

In the present embodiment, a method which uses, for example, the 3G-SDI standard (level B) and which enables transmission with one coaxial cable is used as a method associated with 3D video signals. However, the method is not limited to the 3G-SDI. For HD-SDI and DVI-D video signals, a side-by-side method is described as an example of a 3D format as shown in FIG. 3.

The video signal receiver sections 11 and 12 respectively receive the L and R video signals which have been synchronously output from the first processor 4 and the second processor 5, respectively. The video signal receiver section 11 outputs the L video signal to the selectors 13*a* and 14*a*. The video signal receiver section 12 outputs the R video signal to the selectors 13*a* and 14*a*.

As shown in FIG. 2, when a 3D picture is displayed, the selector 13*a* selects the L video signal, and the selector 14*a* selects the R video signal. When a 2D picture is displayed, both the selectors 13*a* and 14*a* select the L video signal. Here, for the 2D picture, both the selectors 13*a* and 14*a* may select the R video signal. The 3D picture and the 2D picture can be switched by the switch 9*a* or the changeover switch 8.

The video signal (reproduction picture) from the externally connected recorder is received by the video signal receiver section 15. In the case of a picture of the side-by-side method, for example, HD-SDI, the 3D separation section 16 restores the L video signal and the R video signal. In the case of a picture of 3G-SDI, the 3D separation section 16 separates the video signal into the L video signal and the R video signal. The generated L video signal is transmitted to the selector 17, and the generated R video signal is transmitted to the selector 18.

The selector 17 receives the L or R video signal output from the selector 13*a*, and the L video signal output from the 3D separation section 16. The selector 18 receives the L or R video signal output from the selector 14*a*, and the R video signal output from the 3D separation section 16.

In the input switch 108, when a recorded picture is indicated, the signal line is switched so that the video signal of the 3D separation section 16 is input to the selectors 17 and 18, and the selectors 17 and 18 receive the read video data (recorded video signals), and output the video data to the L-picture shift section 19*a* and the R-picture shift section 20*a*.

In contrast, when a camera picture is indicated, the signal line is switched so that the video signals of the selectors 13*a* and 14*a* are input to the selectors 17 and 18, and the selectors 17 and 18 receive the L/R video signals (3D video signals) selected by the selectors 13*a* and 14*a* or the L/L video signals (2D video signals), and respectively output the video signals to the L-picture shift section 19*a* and the R-picture shift section 20*a*.

When 3D picture display (L/R display) is indicated by one of the switches 8 and 9*a*, the L video signal is input to the L-picture shift section 19*a*, and shift processing is performed to move the display position a predetermined distance in a horizontal direction to adjust the display position in a depth direction in the 3D picture. Similarly, the R video signal is input to the R-picture shift section 20*a*, and shift processing is performed to move the display position a predetermined distance in the horizontal direction to adjust the depth display position. The distances to shift the L video signal and the R video signal are set for a predetermined depth position.

In contrast, when 2D picture display (L/L display) is indicated by the above-mentioned switch 9*a* and the 3D/2D picture changeover switch 8, the L video signals are input to both the L-picture shift section 19*a* and the R-picture shift section 20*a*, and both these video signals are shifted 0, that is, are output without being subjected to shift processing.

The respective L and R video signals which have been shift-controlled by the L-picture shift section 19*a* and the R-picture shift section 20*a* are output to the 3D picture composing section 21*a*. Here, the L and R video signals are composed as a 3D video signal in accordance with a preset video signal or a 3D format, and then output to the video signal transmitter 22*a*. The video signal transmitter 22*a* outputs the 3D video signal to the monitor 7 as a video signal. The monitor 7 performs monitor display on the basis of the input video signal.

Specifically, when a 3D picture is selected, the 3D picture composing section 21*a* outputs a video signal to the L/R video signals in a format of 3G-SDI dual stream (level B)

(=HD-SDI×2ch). In contrast, when a 2D picture is selected, the 3D picture composing section 21a outputs a video signal in a format of 3G-SDI dual stream (level B) as the L/L video signals. In this instance, the 2D picture is output with no (zero) shift of the depth position as described above, and is therefore observed as a 2D picture in the monitor 7.

The picture is thus switched between 2D and 3D without the switch of the video signals and the format, so that it is not necessary to switch a video format on the monitor side. As a result, there is no time in which the picture disappears during switching, and it is possible to instantaneously switch between the 2D/3D pictures. Although the 3G-SDI video signals are used in the above description, it is also possible to obtain similar advantages if the side-by-side format is used for the HD-SDI and DVI-D video signals.

Output for the recorder is described.

In the setting control section 109, an unshown menu screen or the like can be used to set whether to link the switch of the 3D/2D pictures with the operation by the changeover switch 9a and the changeover switch 8 (switch linkage) or always set the 3D pictures (constant 3D). When the switch linkage is set, the recorded picture is also switched between the 3D picture and the 2D picture by the switch operation.

In contrast, when the constant 3D display is set, the setting control section 109 cancels the operation by the changeover switch 9a and the changeover switch 8, and controls the selectors 13b and 14b for constant 3D output.

When the picture for recording is also switched between the 3D picture and the 2D picture without the switch of the video signals and the format as described above according to the present invention, it is not necessary to detect or manually switch the 3D format during reproduction by the recorder. Therefore, it is possible to view the recorded picture without any trouble.

Second Embodiment

In the example according to the present embodiment, the 2D/3D pictures are automatically switched by an identification sign ID provided to a video signal. In the present embodiment, components equivalent to those in the first embodiment described above are provided with the same reference signs and are not described.

A payload ID switch section 23 which sends a switch instruction to the 3D picture composing sections 21 in the above-described configuration in FIG. 2 is provided.

In the above-mentioned 3G-SDI dual stream (level B) format, L-picture information and R-picture information are respectively provided to a payload ID in the case of a 3D picture, but, for example, a payload ID for two L-pictures is used in the case of a 2D picture. Thus, it is possible to automatically change the mode of the monitor 7 depending on the 3D picture or the 2D picture, and change color data (the brightness of the screen) regarding the difference of polarized glasses.

Third Embodiment

Figure 4:
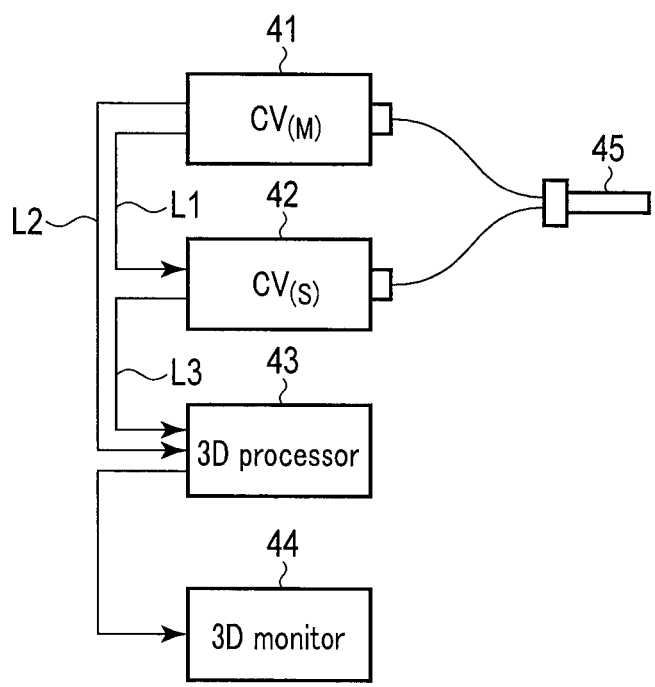
FIG. 4 is a diagram showing a conceptual first configuration example of display switching according to a third embodiment.
Figure 5:
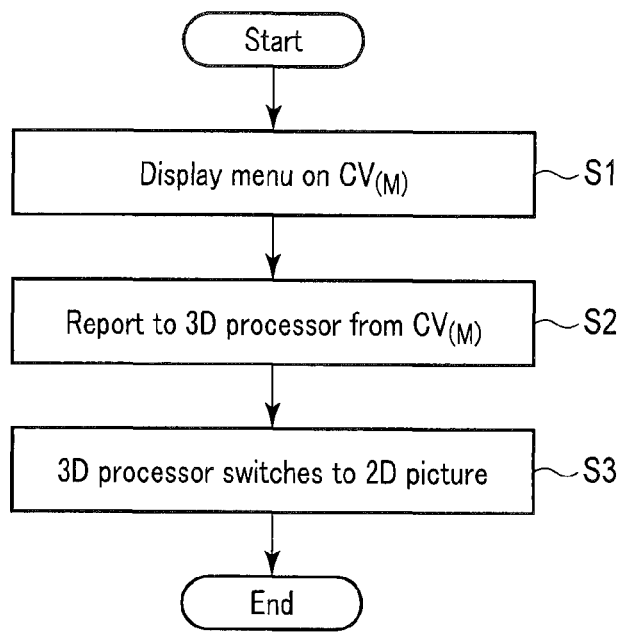
FIG. 5 is a flowchart illustrating a first procedure of display switching according to the third embodiment.

FIG. 4 is a diagram showing a conceptual first configuration example of display switching according to a third embodiment. FIG. 5 is a flowchart illustrating a first procedure of display switching according to the third embodiment. In the present embodiment, the 2D/3D pictures are switched between two processors having a master-servant relationship, and when a preset screen is displayed, the display on the monitor 7 automatically switches from the 3D picture to the 2D picture. In the present embodiment, components equivalent to those in the first embodiment described above are provided with the same reference signs and are not described.

In the present embodiment, between a master processor CV41 and a servant processor CV42, the state of the processor CV41 is reported by a wiring line L1. Both the processor CV41 and the processor CV42 output an L video signal and an R video signal that are synchronized to a 3D processor 43. The 3D processor 43 outputs a 3D video signal and a 2D video signal to a monitor 44, and displays one of the pictures. For example, 2D picture display on a menu screen is set to the processor CV42.

In this configuration, when the processor CV41 is instructed by a user operation to display the menu screen (step S1), the processor CV41 reports to the 3D processor 43 that the menu screen has been displayed (step S2), and the 3D processor switches to the 2D picture. As a result, the menu screen output from the processor CV41 is displayed on the monitor 44 as the menu screen of the 2D picture (step S3).

According to the present embodiment, the 2D picture is used so that there is no (zero) shift of the depth position. Therefore, even staff members without polarized glasses recognize the menu screen as a normal 2D picture, so that these staff members can perform input setting and selecting operations.

Fourth Embodiment

Figure 6:
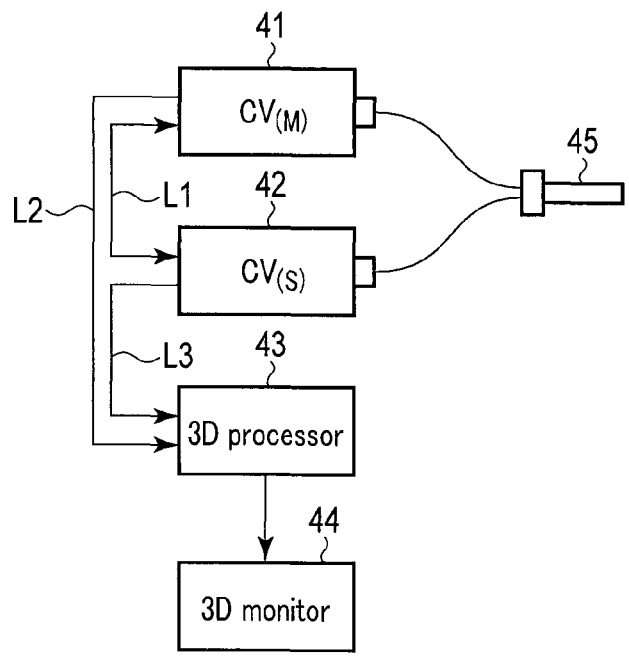
FIG. 6 is a diagram showing a conceptual configuration example of display switching according to a fourth embodiment.
Figure 7:
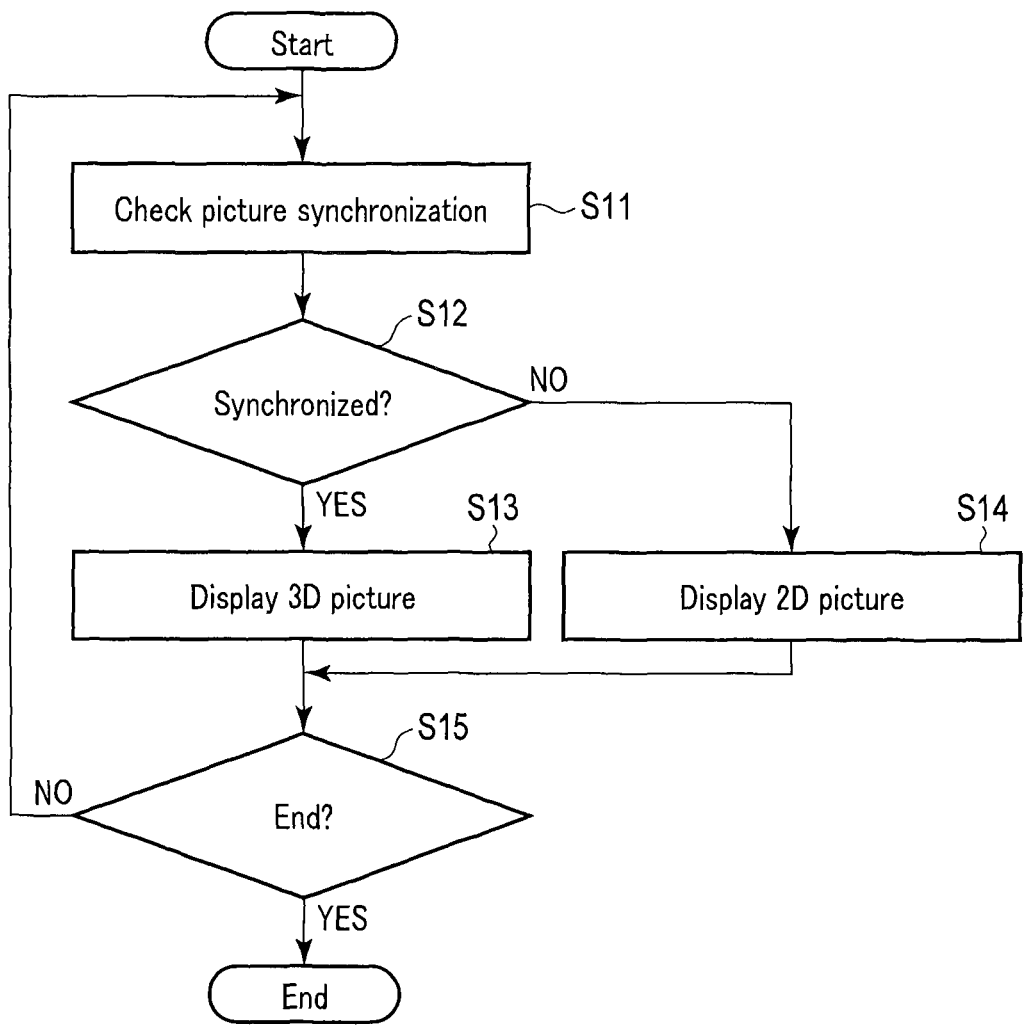
FIG. 7 is a flowchart illustrating a procedure of display switching.

FIG. 6 is a diagram showing a conceptual configuration example of display switching according to a fourth embodiment. FIG. 7 is a flowchart illustrating a procedure of display switching.

In the present embodiment, a communication using a synchronization signal is performed between the two processors CV41 and CV42 having a master-servant relationship for the switch between 2D/3D pictures, and when the 3D processor 43 judges that the processors are not synchronized, the picture which is output from the 3D processor 43 to the monitor 7 is automatically switched from the 3D picture to the 2D picture.

In the present embodiment, synchronization signals are input to the master processor CV41 and the servant processor CV42 by wiring lines L1(M) and L1(S) from the 3D processor 43. Both the processor CV41 and the processor CV42 output an L video signal and an R video signal that are synchronized to the 3D processor 43 (step S11). The 3D processor 43 compares the synchronization signals from the processor CV41 and the processor CV42 (step S12). When the synchronization signals are synchronized (YES), the 3D processor 43 outputs a 3D video signal to the monitor 44 (step S13). When the synchronization signals are not synchronized (NO), the 3D processor 43 switches the 3D video signal to a 2D video signal, and then outputs the 2D video signal to the monitor 44 (step S14). The 3D processor 43 may generate the synchronization signals and outputs the synchronization signals to the processors CV41 and CV42. The 3D processor 43 checks the synchronization signals unless the 3D picture is finished (step S15).

As described above, in the present embodiment, the synchronization of the video signals between the two processors CV41 and CV42 is checked so that the 3D picture is displayed when the video signals are synchronized or the 2D picture is displayed when the video signals are not synchronized.

Therefore, the surgeon is not fatigued with viewing abnormal 3D pictures, which is advantageous to the reduction of the surgeon's fatigue.

Fifth Embodiment

In the present embodiment, the feeling of depth in a 3D picture is changed in accordance with the display size of the screen. The configuration according to the present embodiment uses the above-described configuration shown in FIG. 4.

Normally, when the display size of the screen is changed or when a screen enlarged by electronic zooming is displayed, the depth position is adjusted.

In the present embodiment, a previously found specific value (depth position adjustment value) is set as an adjustment value for the change to a predetermined screen size or for the magnification range in the electronic zooming. As a first example, when the screen size or the magnification is 1.2, the 3D processor displays the preset depth position adjustment value on the monitor 44. This displayed adjustment value is used to adjust the depth position of the screen.

As a second example, for the display of recording, for example, the adjustment value is set to 0 when the screen size or the magnification is 1.0, and when the screen size or the magnification is 1.2, an adjustment value of the depth position corresponding to a difference of 0.2 is displayed on the screen. This displayed adjustment value is used to adjust the depth position of the screen.

The adjustment value is thus displayed on the screen for the change of the screen size or the screen by the electronic zooming, so that an optimum depth position can be set in accordance with the observation state. The difference is only recorded on the basis of a predetermined value, so that when an optimum adjustment is made for the display change in the monitor during reproduction, the electronic zooming is also displayed on the basis of the predetermined value. Therefore, it is possible to view an observation picture which is adjusted to a proper depth position during reproduction as well.

Sixth Embodiment

FIG. 8 is a diagram showing a configuration example of a video mixer unit which performs video processing and display according to a sixth embodiment.

The sixth embodiment shows an endoscopic system which displays an observation image by a 3D picture on a surgeon's monitor and an assistant's monitor. In the case of surgery conducted on a team, an operator and an assistant may be located on two sides across a patient. That is, the assistant faces the operator on the opposite side. During surgery, the assistant also has to observe a treatment target. Thus, a photography element for the assistant can be incorporated into the endoscope, but this method leads to the size increase and cost increase of the scope. In contrast, when a 3d picture for the surgeon is used, a reverse picture in which the right and left are simply interchanged becomes a reverse stereoscopic picture.

Thus, the configuration according to the present embodiment has two video lines: a surgeon's 2D/3D video line and an assistant's 2D/3D video line. In particular, the assistant's video line comprises a picture rotation section which rotates a picture 180 degrees. In the present embodiment, components equivalent to those in the first embodiment described above are provided with the same reference signs (however, with a and b) and are not described.

As shown in FIG. 8, the video mixer unit 6 comprises, as the surgeon's video line, photography signal conversion sections 31 and 32 which receive L and R video signals output from the photography element and convert the L and R video signals into digital video signals, two pairs of selectors 13a and 14a and 17a and 18a, the picture shift sections 19a and 20a, the 3D picture composing section 21a, the video signal transmitter 22a, and a surgeon's monitor 7a. The video mixer unit 6 also comprises, as the assistant's video line, picture rotation sections 33 and 34 which rotate 180 degrees the L and R video signals output from the photography signal conversion sections 31 and 32, two pairs of selectors 13b and 14b and 17b and 18b, the picture shift sections 19b and 20b, the 3D picture composing section 21b, a video signal transmitter 22b, and an assistant's monitor 7b.

Regarding the surgeon's video line, the processing of video signals subsequent to the photography signal conversion sections 31 and 32 is equivalent to that in the first embodiment described above, and is therefore not described.

In the assistant's video line, the L and R video signals which have been converted in the photography signal conversion sections 31 and 32 are input to the picture rotation sections 33 and 34. The picture rotation sections 33 and 34 use a known conversion technique to generate a rotated L-picture (signal) and a rotated R-picture (signal) in which the L-picture and the R-picture are rotated 180 degrees. These pictures are rotated around vertical axes (perpendicular lines in the pictures) 180 degrees. The rotated L-picture and the rotated R-picture are horizontally rearranged to set a new L video signal (original rotated R video signal) and a new R video signal (original rotated L video signal). The pictures are interchanged in the new L and R video signals by the selectors 13b and 14b, and shift processing and composing processing equivalent to those in the first embodiment described are performed by the picture shift sections 19b and 20b, the 3D picture composing section 21b, and the video signal transmitter 22b, and then a reversed 3D video observation target is displayed on the assistant's monitor 7b.

In the present embodiment as well, a recorder can be externally connected, and the screen can be displayed by a reproduction operation. When a recorded picture is indicated in the surgeon's video line, the selectors 17a and 18a switch the signal lines so that the video signal of the 3D separation section 16 is input, and the selectors 17a and 18a receive the read video data (recorded video signals), and output the video data to the L-picture shift section 19a and the R-picture shift section 20a. Further, the 3D picture composing section 21a and the video signal transmitter 22a perform shift processing and composing processing equivalent to those in the first embodiment described, and a reversed observation target is displayed on the assistant's monitor 7b. The same also applies to the assistant's video line.

As in the second embodiment, the payload switch section 23 is provided, and the 2D/3D pictures can be switched on the basis of a retrieved payload ID. When a 3D picture is displayed by the payload ID, it is also possible to automatically change the mode of the monitor 7 and change color data (the brightness of the screen) regarding the difference of polarized glasses.

According to the present embodiment, not only the surgeon but also the assistant located on the opposite side can view the picture of the observation target based on the assistant.

Seventh Embodiment

The configuration according to the present embodiment is equivalent to the configuration shown in FIG. 1 and FIG. 2, but is different in that the scope connectors have identification (ID) information.

The L/R scope connectors 25 and 26 according to the present embodiment have therein authentication sections having the ID information that varies depending on the L video signal and the R video signal to be transmitted.

The configuration according to the present embodiment interchanges the L/R pictures when the L/R of the scope connectors connected to the two processors are interchanged. Normally, the L scope connector to which the L video signal is transmitted is attached to the first processor 4, and the R scope connector to which the R video signal is transmitted is attached to the second processor 5.

However, suppose that the user mistakes the L/R connections and attaches the L scope connector 25 to the second processor 5 and attaches the R scope connector 26 to the first processor 4.

In the case of such erroneous connection, the first processor 4 outputs the ID information read from the R scope connector 26 to the video mixer unit 6. Similarly, the second processor 5 outputs the ID information read from the L scope connector 25 to the video mixer unit 6.

The video mixer unit 6 judges from the ID information that the L/R of the connector connection are reversed. On the basis of this judgment, the L video signal and the R video signal which are output from the selectors 13a and 14a shown in FIG. 2 are interchanged. That is, in the ordinary selection for normal connector connection, the L video signal is output from the selector 13a, and the R video signal is output from the selector 14a. On the contrary, when the connectors are reversely connected (erroneously connected) and a normal selection is made, the R video signal is output from the selector 13a, and the L video signal is output from the selector 14a. Thus, if a reverse selection is made, the L video signal is output from the selector 13a, and the R video signal sent from the selector 14a.

According to the present embodiment, the authentication sections having the ID information are provided inside the connectors. Therefore, it is possible to connect the scope connectors without paying attention to the connection of their L/R in contrast to conventional connection. Moreover, even erroneous connection is automatically judged and corrected, and a picture with correct right and left is displayed on the screen.

Furthermore, "device names" and "serial numbers" can be incorporated in the authentication sections inside the scope connectors so that when more than one 3D endoscopes are used, a wrong combination can be displayed on the monitor or reported with an alert sound to urge the user to make correct connection.

Eighth Embodiment

FIGS. 9A and 9B are diagrams illustrating the easily viewable observation image by a 3D picture according to an eighth embodiment. The 3D picture is displayed on the display screen of the monitor with the feeling of backward and forward depth, and there is a range in which this feeling of depth can be easily viewed and observed. Beyond this range and with an extremely small depth, the feeling of depth is extremely hard to view. The 3D picture with an extremely small depth is often used in, for example, industrial promotions, and gives tension and causes the sense of fatigue. In contrast, an extreme great depth causes the observation axes of both eyes to open in a direction to split wider the parallel state, and it is also extremely hard to view.

The present embodiment provides a space (shift value) between the L-picture and the R-picture displayed on the monitor set in association with the value of the display magnification in the monitor. The space is set to the value of a substantially split angle (a nominal value at which the space between a left-eye optical axis 72 and a right-eye optical axis 73 of the user is the same as the shift value (space) of the separate left and right pictures on the monitor) at which an observation target part 74 located L=100 mm ahead is observed from the distal end face of an insertion portion 71 of an endoscope shown in FIGS. 9A and 9B where an objective lens of the photography unit is located.

As shown in FIG. 9B, when the distance to the monitor screen is L, the range in which the 3D picture of the observation target part 74 is easily viewable is a range M which is 0.15 L on the near side and which is 0.3 L on the far side.

As shown in FIG. 9A, when the right-eye and left-eye optical axes intersect at one point of the observation target part, the position where the 3D picture is formed on the 3D monitor is configured so that the intersection of the right and left optical axes is located on the monitor if the central position of L and R pictures 76 are displayed to correspond to the position of the monitor screen. In this case, it is easier to come out of the easily viewable range on the nearer side. In contrast, when the central position is farther from the position of the monitor screen as in L and R pictures 77, the picture is displayed on the farther side, and the feeling of depth increases. However, if the optical axis is too far, the eyes become tired. In zooming as well, the 3D picture may exceed the easily viewable range if enlarged too much and displayed.

Figure 10A:
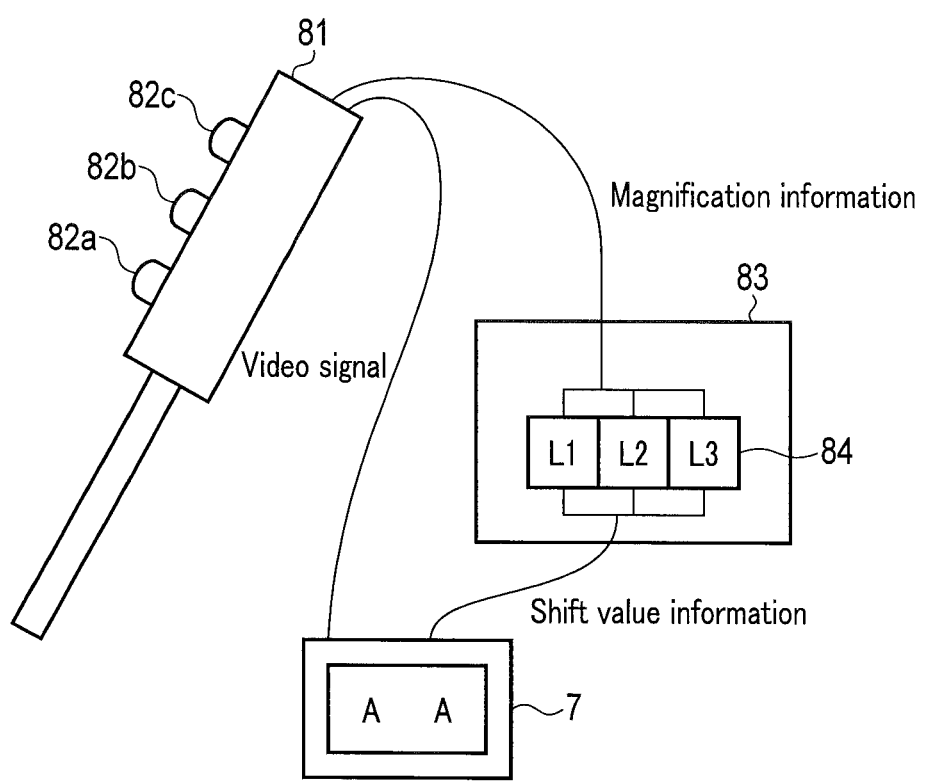
FIG. 10A is a diagram illustrating a configuration for zooming an observation image and a display screen.
Figure 10B:
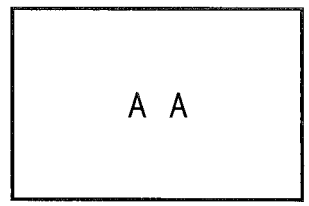
FIG. 10B is a diagram illustrating the configuration for zooming the observation image and the display screen.
Figure 10C:
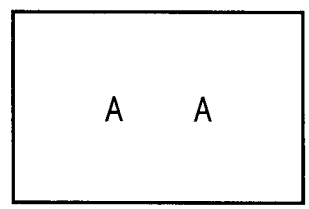
FIG. 10C is a diagram illustrating the configuration for zooming the observation image and the display screen.
Figure 10D:
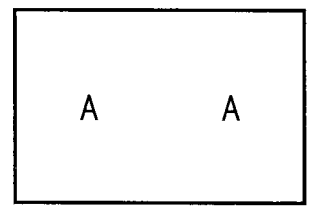
FIG. 10D is a diagram illustrating the configuration for zooming the observation image and the display screen.

In FIG. 10A, shift values for the L and R pictures are previously set for a magnification $\beta$ in the 3D picture. For example, zoom magnifications (shift values) corresponding to operation switches 82a, 82b, and 82c of an operation portion 81 are set. Here, the magnification $\beta=1$ shown in FIG. 10B is set by the operation of the operation switch 82a, and the magnification $\beta=1.2$ shown in FIG. 10B is set by the operation of the operation switch 82b. Similarly, the magnification $\beta=1.5$ shown in FIG. 10C is set by the operation of the operation switch 82c.

Thus, if the 3D picture is electronically zoomed in by the operation of the zoom switching operation switches 82a, 82b, and 82c provided in the operation portion 81, the shift value information previously set in a memory 84 is read, and on the basis of the shift values, the L and R pictures displayed on the monitor 7 can be shifted and displayed on the monitor screen within the easily viewable range.

Thus, according to the present embodiment, it is possible to easily view a zoomed picture which is enlarged for easy viewing by a simple operation.

The embodiments described above include the following contents of the invention.

An endoscopic system characterized by comprising:
an endoscope having an insertion portion to be inserted into a lumen;
a photography unit which is provided in parallel with the distal end face of the insertion portion and which acquires a right picture and a left picture;
a switch section which selects the right picture and the left picture output from the photography unit and which performs a first selection to select a pair of the right picture and the left picture and a second selection to select one of the right picture and the left picture;
 a processor section which performs shift processing for the right picture and the left picture selected by the first selection in the switch section so that the space between the right picture and the left picture becomes a predetermined distance, and generates a stereoscopic picture; and
 a display section which displays one of the right picture and the left picture by the switching of the switch section,
 wherein when switching from the first selection to the second selection, the switch section holds connection to continue the display of one of the right picture and the left picture, cuts off the display of the other picture, or replaces the display of the one picture with the display of the other picture, and
 when switching from the second selection to the first selection, the switch section continues the display of one of the pictures on the display section, and after the picture which is different from the above picture and which is not displayed is selected and the shift processing is performed between this picture and the picture displayed in the processor section, the switch section displays the picture on the display section.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An endoscopic system comprising:
 an endoscope configured to acquire each of right-eye and left-eye optical images to generate right-eye and left-eye imaging signals which indicate the respective right-eye and left-eye optical images;
 a first processor configured to convert the right-eye imaging signal into a right-eye video signal;
 a second processor configured to convert the left-eye imaging signal into a left-eye video signal;
 a video mixer unit to which each of the video signals is input from the endoscope, the video mixer unit being configured to output either one of a stereoscopic video signal based on both the right-eye and left eye video signals and a planar video signal based only on one of the right-eye and left-eye video signals; and
 a switch configured to, upon operation by a user, output an instruction signal to instruct which of the stereoscopic video signal and the planar video signal is output from the video mixer unit,
 wherein the video mixer unit comprises;
  a first selector configured to select one of the right-eye video signal and the left-eye video signal;
  a second selector configured to select one of the right-eye video signal and the left-eye video signal that is not selected by the first selector if the instruction signal from the switch instructs to output the stereoscopic video signal, and to select one of the right-eye video signal and the left-eye video signal that is the same as the video signal selected by the first selector if the instruction signal from the switch instructs to output the planar video signal;
  a first picture shift circuit configured to horizontally shift the video signal selected by the first selector according to a given shift value;
  a second picture shift circuit configured to horizontally shift the video signal selected by the second selector according to a given shift value;
  a picture composing circuit configured to synthesize the video signal from the first picture shift circuit with the video signal from the second picture shift circuit to generate a 3D format video signal; and
  a video signal transmitter configured to output the 3D format video signal to a monitor,
 wherein the first picture shift circuit is given a shift value for horizontally shifting the video signal selected by the first selector if the instruction signal from the switch instructs to output the stereoscopic video signal, and is given a shift value indicative of not subjecting the video signal selected by the first selector to the horizontal shifting if the instruction signal from the switch instructs to output the planar video signal,
 wherein the second picture shift circuit is given a shift value for horizontally shifting the video signal selected by the second selector to provide the video signal with a parallax to the video signal selected by the first selector if the instruction signal from the switch instructs to output the stereoscopic video signal, and is given a shift value indicative of not subjecting the video signal selected by the second selector to the horizontal shifting if the instruction signal from the switch instructs to output the planar video signal, and
 wherein the picture composing circuit is configured to:
  generate the 3D format video signal for the video signal subjected to the shifting at and output from each of the first picture shift circuit and the second picture shift circuit if the instruction signal from the switch instructs to output the stereoscopic video signal; and
  generate the 3D format video signal for the video signal not subjected to the shifting at and output from each of the first picture shift circuit and the second picture shift circuit if the instruction signal from the switch instructs to output the planar video signal.

2. The endoscopic system according to claim 1, wherein the 3D format video signal from the picture composing circuit is output to a picture recorder.

3. The endoscopic system according to claim 1, wherein the video signal transmitter is configured to output the 3D format video signal by a side-by-side method.

4. The endoscopic system according to claim 2, wherein the picture recorder is configured to record the 3D format video signal of a side-by-side method output from the video signal transmitter.

5. The endoscopic system according to claim 1, wherein the switch is provided in at least one of a handle of the endoscope or the video mixer unit.

6. The endoscopic system according to claim 1, further comprising:
 a display configured to input the 3D format video signal output from the video signal transmitter and then to display a picture based on the 3D format video signal,
 wherein the first picture shift circuit is configured to perform shift processing for the right-eye video signal or the left-eye video signal selected by the first selector so that the right-eye video signal and the left-eye video signal has a predetermined distance therebetween,
 wherein when the instruction signal is switched from instructing output of the stereoscopic video signal to instructing output of the planar video signal, the first selector is configured to continue the selection of one of the right-eye video signal and the left-eye video signal, and the second selector is configured to cut off the selection of the other video signal or replace the selection of the one video signal with the selection of the other video signal, and wherein when the instruction signal is switched from instructing output of the planar video signal to instructing output of the stereoscopic video signal, the display is configured to continue displaying the picture, and after another 3D format video signal is output based on the selection of the different video signal at the second selector and the shift processing at the second picture shift circuit, the display is configured to display a picture based on the another 3D format video signal.

7. The endoscopic system according to claim 2, further comprising:
  a second switch configured to, upon operation by a user, output a second instruction signal to instruct whether the 3D format video signal generated by the picture composing circuit is output from the video signal transmitter or the 3D format video signal recorded in the picture recorder is output;
  a third selector configured to select output of the video signal selected by the first selector or output of a left-eye video signal component of the 3D format video signal input from the picture recorder, according to the second instruction signal from the second switch; and
  a fourth selector configured to select output of the video signal selected by the second selector or output of a right-eye video signal component of the 3D format video signal input from the picture recorder, according to the second instruction signal from the second switch.

8. An endoscopic system comprising:
  an endoscope configured to acquire each of right-eye and left-eye optical images to generate right-eye and left-eye imaging signals which indicate the respective right-eye and left-eye optical images;
  a first imaging signal conversion circuit configured to convert the right-eye imaging signal into a right-eye video signal;
  a second imaging signal conversion circuit configured to convert the left-eye imaging signal into a left-eye video signal;
  a video mixer unit to which each of the video signals is input from the endoscope, the video mixer unit being configured to output either one of a stereoscopic video signal based on both the right-eye and left eye video signals and a planar video signal based only on one of the right-eye and left-eye video signals; and
  a switch configured to, upon operation by a user, output an instruction signal to instruct which of the stereoscopic video signal and the planar video signal is output from the video mixer unit, wherein the video mixer unit comprises;
  a first selector configured to select one of the right-eye video signal and the left-eye video signal;
  a second selector configured to select one of the right-eye video signal and the left-eye video signal that is not selected by the first selector if the instruction signal from the switch instructs to output the stereoscopic video signal, and to select one of the right-eye video signal and the left-eye video signal that is the same as the video signal selected by the first selector if the instruction signal from the switch instructs to output the planar video signal;
  a first picture shift circuit configured to horizontally shift the video signal selected by the first selector according to a given shift value;
  a second picture shift circuit configured to horizontally shift the video signal selected by the second selector according to a given shift value;
  a picture composing circuit configured to synthesize the video signal from the first picture shift circuit with the video signal from the second picture shift circuit to generate a 3D format video signal; and
  a video signal transmitter configured to output the 3D format video signal to a monitor, wherein the first picture shift circuit is given a shift value for horizontally shifting the video signal selected by the first selector if the instruction signal from the switch instructs to output the stereoscopic video signal, and is given a shift value indicative of not subjecting the video signal selected by the first selector to the horizontal shifting if the instruction signal from the switch instructs to output the planar video signal, wherein the second picture shift circuit is given a shift value for horizontally shifting the video signal selected by the second selector to provide the video signal with a parallax to the video signal selected by the first selector if the instruction signal from the switch instructs to output the stereoscopic video signal, and is given a shift value indicative of not subjecting the video signal selected by the second selector to the horizontal shifting if the instruction signal from the switch instructs to output the planar video signal, and wherein the picture composing circuit is configured to:
  generate the 3D format video signal for the video signal subjected to the shifting at and output from each of the first picture shift circuit and the second picture shift circuit if the instruction signal from the switch instructs to output the stereoscopic video signal; and
  generate the 3D format video signal for the video signal not subjected to the shifting at and output from each of the first picture shift circuit and the second picture shift circuit if the instruction signal from the switch instructs to output the planar video signal.

* * * * *